United States Patent [19]

Caspari et al.

[11] Patent Number: 4,923,461
[45] Date of Patent: May 8, 1990

[54] METHOD OF ARTHROSCOPIC SUTURING OF TISSUE

[75] Inventors: Richard B. Caspari, Maidens, Va.; Arthur F. Trott, Largo; F. Barry Bays, Seminole, both of Fla.

[73] Assignee: Concept, Inc., Largo, Fla.

[21] Appl. No.: 326,991

[22] Filed: Mar. 22, 1989

Related U.S. Application Data

[62] Division of Ser. No. 117,158, Nov. 5, 1987, Pat. No. 4,890,615.

[51] Int. Cl.⁵ .............................................. A61B 17/00
[52] U.S. Cl. ...................................... 606/146; 606/148
[58] Field of Search ................. 128/334 R, 335, 339, 128/340; 606/146, 148

[56] References Cited

U.S. PATENT DOCUMENTS

| | | | |
|---|---|---|---|
| 919,138 | 4/1909 | Drake et al. | 128/340 |
| 1,815,725 | 2/1930 | Pilling et al. | 128/340 |
| 3,013,559 | 12/1961 | Thomas | 128/340 |
| 3,470,875 | 10/1969 | Johnson | 128/340 |
| 3,638,653 | 2/1972 | Berry | 128/340 |
| 3,840,017 | 10/1974 | Violante | 128/340 |
| 3,842,840 | 10/1974 | Schweizer | 128/340 |
| 3,901,244 | 8/1975 | Schweizer | 128/334 R |
| 3,946,740 | 3/1976 | Bassett | 128/340 |
| 4,164,225 | 8/1979 | Johnson et al. | 128/340 |
| 4,224,947 | 9/1980 | Fukuda | 128/340 |
| 4,312,337 | 11/1982 | Donohue | 128/340 |
| 4,493,323 | 1/1985 | Albright et al. | 128/340 |
| 4,596,249 | 6/1986 | Freda et al. | 128/340 |
| 4,602,635 | 7/1986 | Mulhollan et al. | 128/340 |
| 4,621,640 | 11/1986 | Mulhollan et al. | 128/334 R |
| 4,643,178 | 2/1987 | Nastari et al. | 128/92 VK |
| 4,781,190 | 11/1988 | Lee | 128/339 |

*Primary Examiner*—Randall L. Green
*Assistant Examiner*—Gary Jackson
*Attorney, Agent, or Firm*—Epstein, Edell & Retzer

[57] ABSTRACT

A method of suturing tissue in the body particularly useful in arthroscopic surgery requiring only small incisions or portals for insertion of diagnostic and surgical instruments includes the steps of inserting an instrument in the body having a distal end carrying relatively movable jaws with openings therein, manipulating the jaws to penetrate the tissue to be sutured and to move the jaws to positions adjacent each other with the openings therein aligned, feeding suture material through the openings in the jaws, securing ends of the suture material to form a knot and moving the knot to a position adjacent the tissue.

8 Claims, 3 Drawing Sheets

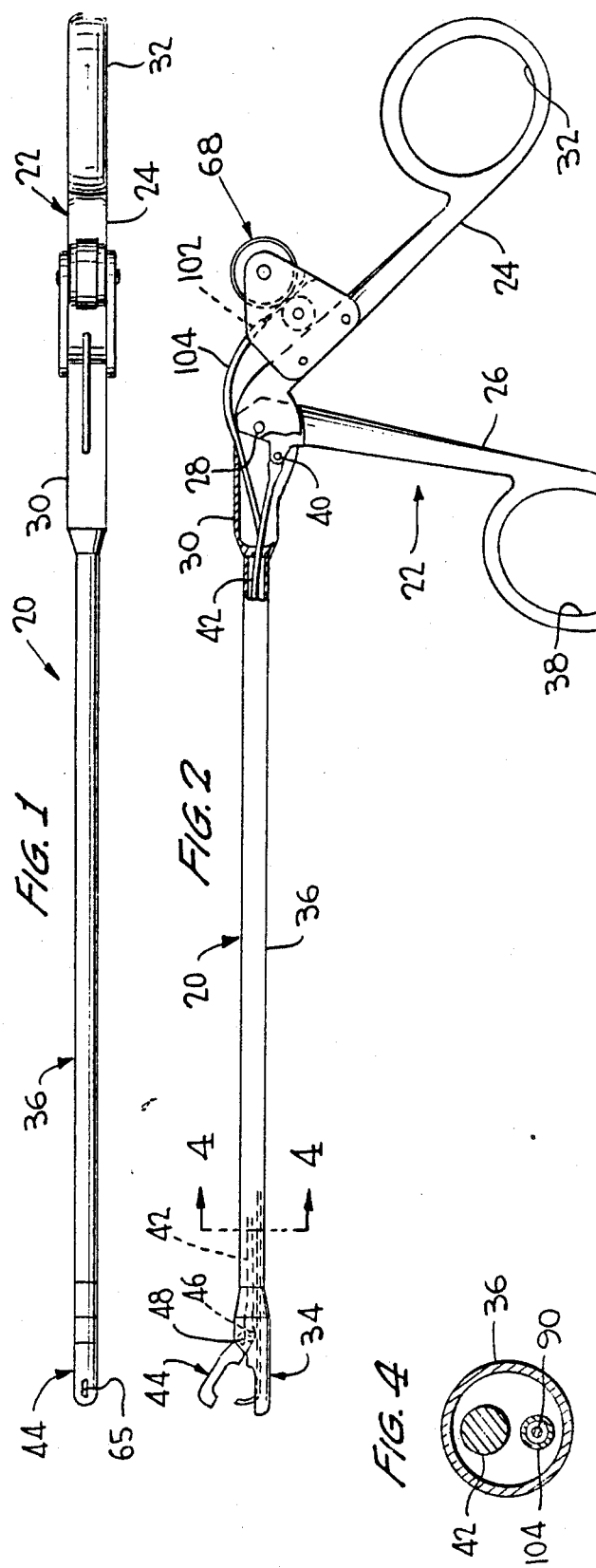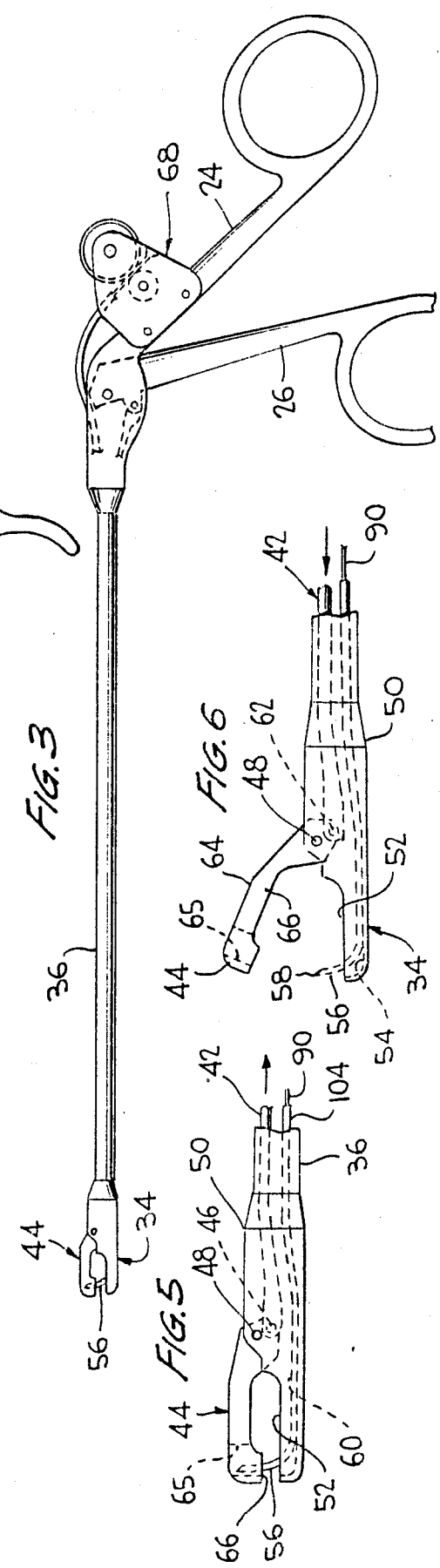

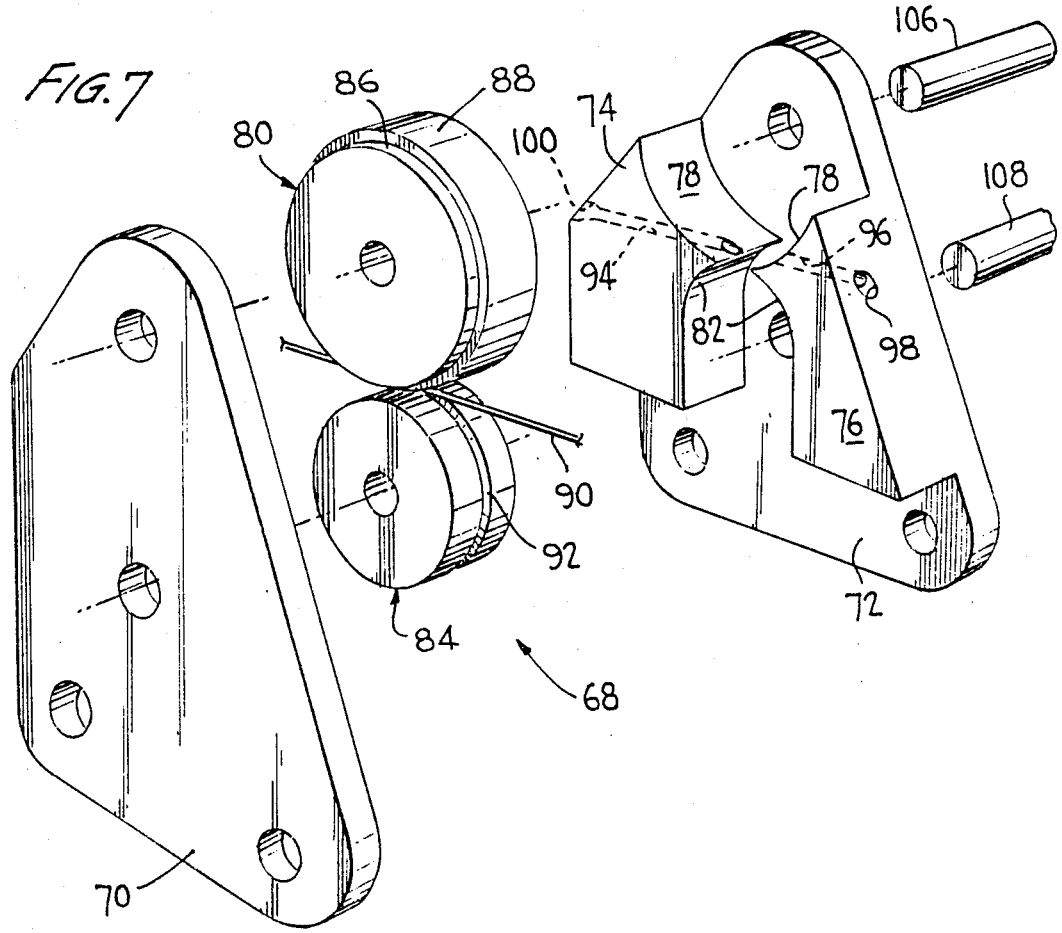

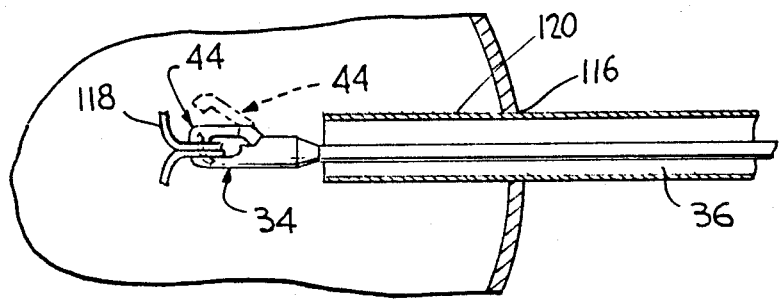
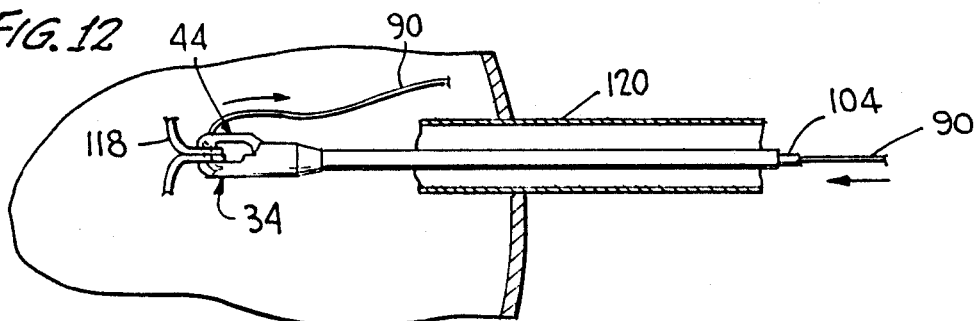
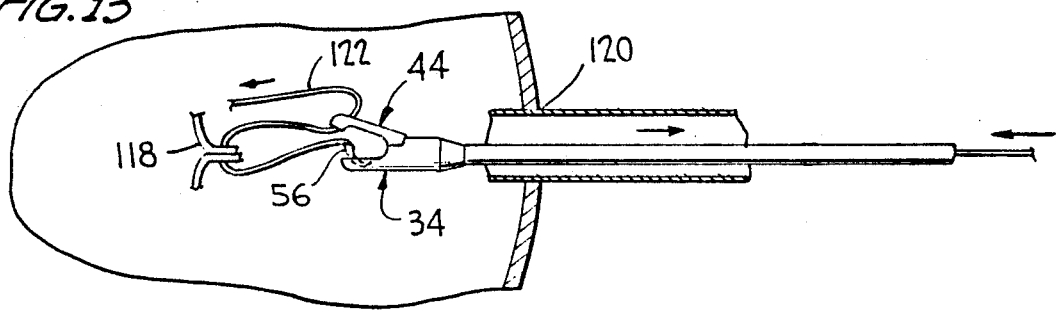
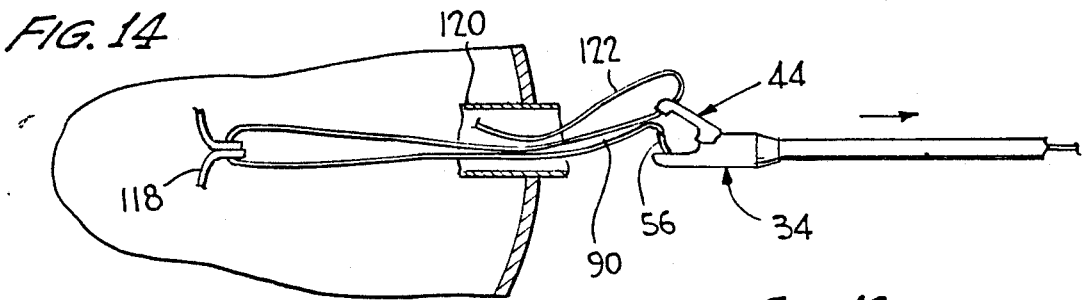
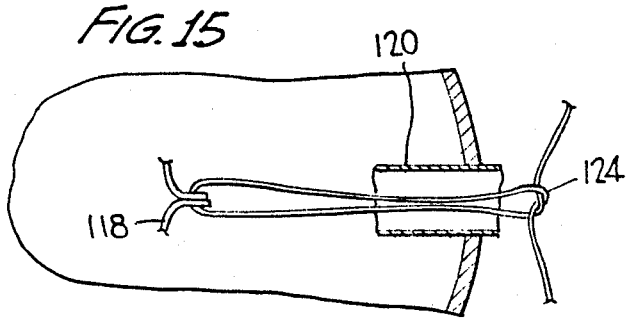
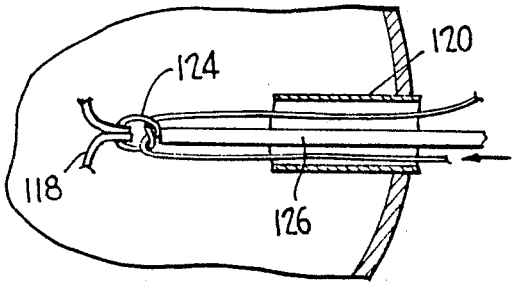

METHOD OF ARTHROSCOPIC SUTURING OF TISSUE

This application is a division of application Ser. No. 07/117,158 filed Nov. 5, 1987 now Pat. No. 4,890,615.

BACKGROUND OF THE INVENTION

1. Field of the Invention

The present invention pertains to suturing instruments and, more particularly, to instruments for arthroscopic suturing of tissue within the body without requiring open surgery.

2. Discussion of the Prior Art

Arthroscopic surgery, which is used herein to encompass surgery on various parts of the body requiring only small incisions or portals for insertion of diagnostic and surgical instruments manipulated externally of the body as well as such surgery performed on joints, is preferable over open surgery to avoid the trauma associated with large incisions as well as the hospitalization and prolonged recovery periods required with open surgery and is used whenever possible to achieve the sam results as open surgery without the disadvantages thereof. Arthroscopic techniques include internal viewing for diagnosis and identification of problems as well as surgical operations such as meniscus removal or repair, shaving of irregular, roughened patella and other surfaces and articular surface smoothing. While many surgical operations that previously required open surgery can now be performed by arthroscopic surgery, there remain operations that still require open surgery due to the need for direct suturing, such as major ligament repair and cartilage repair.

U.S. Pat. Nos. 4,493,323 to Albright et al, and Nos. 4,602,635 and 4,621,640 to Mulhollan et al are representative of prior art instruments for internal suturing without requiring open surgery; however, such instruments have the disadvantages of requiring multiple instrument manipulation and movement of needles carrying sutures entirely through tissue to be sutured. The instrument of the Albright et al patent includes a pair of needles forced outwardly through the end of a tube by a plunger to penetrate and extend through the tissue to be sutured and through the skin to permit the needles to be grasped by the surgeon and pulled to position a suture thread loop attached to the needles. The instrument of the Mulhollan et al Pat. No. 4,621,640 includes a curved needle carried by a pivotal head movable to cause the needle to be set in the tissue to be sutured, the needle then being released and the instrument withdrawn to allow insertion of another instrument to pull the needle through. The Mulhollan et al Pat. No. 4,602,635 relates to an instrument for tying knots in sutures in a manipulation area external of the body after the sutures are sewn through the tissue and then pushing the knots into place adjacent the tissue.

U.S. Pat. Nos. 919,138 to Drake et al, No. 3,840,017 to Violante, No. 4,224,947 to Fukuda, and No. 4,643,178 to Nastari et al are representative of prior art suturing instruments wherein sutures are passed through hollow needles after the needles penetrate through tissue to be sutured, such suturing instruments having the disadvantage of requiring grasping of the suture material and, thus, being useful only in open surgery and not in arthroscopic surgery.

U.S. Pat. No. 1,815,725 to Pilling et al, U.S. Pat. No. 3,470,875 to Johnson, U.S. Pat. No. 3,842,840 to Schweizer, U.S. Pat. No. 3,946,740 to Bassett and U.S. Pat. No. 4,164,225 to Johnson et al are representative of prior art suturing instruments having pivoted, scissor-like arms with a needle forced through the end of one arm, through tissue to be sutured and into the end of the other arm where the suture is grasped or clamped, such suturing instruments having the disadvantage of being of a structural design to prevent their use in arthroscopic surgery.

U.S. Pat. No. 4,312,337 to Donohue discloses an instrument for drilling and wiring bones having scissor-like arms carrying cannula sections through which a wire is passed, the wire being cut and tied after the cannula sections are withdrawn. The scissor-like structure permits this instrument to be used only in open surgery and not in arthroscopic surgery.

Another scissor-like instrument for suturing is disclosed in U.S. Pat. No. 4,596,249 to Freda et al, the instrument having a hook passing through tissue to engage a suture and pull it back through the tissue, the instrument not being useful in arthroscopic surgery due to its scissor-like structure.

SUMMARY OF THE INVENTION

Accordingly, it is a primary object of the present invention to overcome the disadvantages of the prior art by providing a method of suturing for use in arthroscopic surgery.

Another object of the present invention is to permit suturing during surgery with an instrument that can be introduced through an arthroscopic tube or cannula to set a suture in tissue and withdrawn to permit tying of a knot and tightening of the knot adjacent the tissue.

A further object of the present invention is to permit setting of sutures during arthroscopic surgery with manipulation by a surgeon in a manner similar to a conventional grasper or forceps.

The present invention has another object in that suture material can be fed through a hollow needle after the needle has been forced through tissue to be sutured allowing the suture material to be pulled from the body, a knot tied therein and the knot moved back into the body adjacent the tissue.

Some of the advantages of the present invention over the prior art are that suturing can be accomplished without requiring open surgery, the suturing instrument is simple in structure facilitating its use in surgery, and the suturing instrument permits accurate placement of sutures by the jaws clamping tissue to be sutured while the hollow needle penetrates the tissue.

The present invention is generally characterized in a method of arthroscopic suturing of tissue within the body including the steps of penetrating tissue to be sutured with a hollow needle, feeding suture material through the hollow needle to define a free end segment of the suture material extending from the hollow needle, withdrawing the hollow needle from the tissue and from the body, pulling the free end segment of the suture material from the body, tying a knot in the suture material externally of the body, and moving the knot into the body to a position adjacent the tissue.

Other objects and advantages of the present invention will become apparent from the following description of the preferred embodiment taken in conjunction with the accompanying drawings.

BRIEF DESCRIPTION OF THE DRAWINGS

FIG. 1 is a top view of a suturing instrument according to the present invention.

FIGS. 2 and 3 are side elevations of the suturing instrument of the present invention with the jaws in open and closed positions, respectively.

FIG. 4 is a sectional view taken along line 4—4 of FIG. 2.

FIGS. 5 and 6 are broken side views of the jaws of the suturing instrument of the present invention in closed and open positions, respectively.

FIG. 7 is an exploded view of the suture feed mechanism of the suturing instrument of the present invention.

FIGS. 8, 9 and 10 are top views of right-hand, straight and left-hand jaw tips for the suturing instrument of the present invention.

FIGS. 11, 12, 13, 14 15 and 16 illustrate the method of use of the suturing instrument of the present invention.

DESCRIPTION OF THE PREFERRED EMBODIMENT

A suturing instrument 20 according to the present invention is illustrated in FIGS. 1, 2 and 3 and includes a handle 22 formed of a stationary handle member 24 and a movable handle member 26 pivotally mounted to stationary handle member 24 on a pivot pin 28 secured in a hub 30. The stationary handle member 24 has a thumb ring 32 at one end and forms part of a stationary member including hub 30, a distal stationary jaw 34 and an elongate tube or barrel 36. The movable handle member 26 has a finger ring 38 at one end and extends through an opening in the bottom of the hub to be mounted on pivot pin 28. A flange 40 extends distally from movable handle member 26 and is pivotally attached to a connector rod 42 extending within tube 36 to the distal end thereof where the rod is connected to a pivotal jaw 44 via a pin 46, the jaw 44 being pivotally mounted on a pin 48 secured to the stationary jaw 34 to pivot toward and away from the stationary jaw. The stationary and movable handle members and the elongate tube terminating at a distal end in a jaw tip are structurally similar to conventional grasper and forceps-type microsurgical instruments commonly used for arthroscopic surgery.

In accordance with the present invention, the stationary jaw 34 includes a hollow tip 50, as best shown in FIGS. 5 and 6, secured to the distal end of tube 36, the tip being cut away to define a peripheral wall 52 for engaging tissue to be sutured and a recess 54 in which is secured a hollow, tubular needle 56 having a bevelled cutting tip 58 to penetrate tissue to be sutured. The needle 56 is smoothly curved such that the portion terminating at tip 58 extends substantially transversely from a portion 60 secured in recess 54 and, thus, extends substantially transversely from the plane of the ends of the peripheral wall 52 of the stationary jaw. Pivotal jaw 44 is pivotally mounted to tip 50 on pin 48 and has an inner end 62 attached to rod 42 via pin 46 and an outer end 64 with an aperture 65 therethrough aligned with needle 56 such that needle tip 58 will extend into the aperture when the jaws are closed as shown in FIG. 5. The pivotal jaw 44 has an inner surface 66 facing the surface of peripheral wall 52 of the stationary jaw such that tissue to be sutured can be clamped between surfaces 52 and 66 when the jaws are closed.

A suture feed mechanism 68 is mounted on stationary handle member 24 and includes, as best shown in FIG. 7, mounting plates 70 and 72 having a pair of spaced lower holes to receive screws to secure the plates to opposite sides of the stationary member. Mounting plate 72 has bosses 74 and 76 thereon to define curved upper surfaces 78 forming a recess for receiving a drive roller 80 and curved lower surfaces 82 forming a recess for receiving an idler roller 84. Roller 80 has opposite side flanges 86 forming an central channel receiving a peripheral ring 88 of high friction, autoclavable material, such as silicone rubber, for engaging a suture material 90 that passes between rollers 80 and 84 riding in a peripheral, V-shaped groove 92 in roller 84. Aligned bores 94 and 96 extend through bosses 74 and 76, respectively, to guide suture material 90 therethrough with bore 96 having a countersunk outlet 100 to receive the proximal end 102 of a length of tubing 104 that runs through an opening in the top of hub 30 and through tube 36 below rod 42, as shown in FIGS. 2 and 4, to terminate at needle 56. Needle 56 and tubing 104 can be formed of single length of stainless steel tubing or can be two pieces joined at the distal end of the suturing instrument 20. Rollers 80 and 84 are rotatably mounted on pins 106 and 108, respectively, secured in holes in plates 70 and 72.

With the exception of ring 88, all components of the suturing instrument 20 are preferably constructed of stainless steel; and, with the ring made of silicone rubber, the entire instrument is autoclavable.

The jaws of the suturing instrument can extend from the distal end of the tube 36 in alignment with the longitudinal axis thereof, as described above and shown at 110 in FIG. 9, or can be bent to the right or left, as shown in FIGS. 8 and 10, at 112 and 114, respectively, to extend at an angle to the longitudinal axis of tube 36. The pivot pins 46 and 48 are positioned at the same place in the straight, right hand and left hand configurations with the stationary and pivotal jaws bent beyond pivot pin 48. Aperture 65 in the pivotal jaws are oblong to facilitate accommodation of the needle 56 when the jaws are closed clamping tissue to be sutured therebetween. While an aperture is preferred to increase structural integrity of the pivotal jaw, an opening of any shape, such as a slot, can be used.

Use and operation of the suturing instrument will be described with reference to FIGS. 11-16. The suturing instrument 20 is inserted into the body through an incision or portal 116 in the skin and moved to the tissue to be sutured 118. In most cases, the suturing instrument will be inserted through a tube or cannula 120, and positioning of the suturing instrument is accomplished using conventional arthroscopic instruments which permit television viewing of the surgical site for inspection, diagnosis and surgery. The jaws are opened by pivoting movable handle member 26 away from stationary handle member 24 using the finger and thumb, respectively, to cause pivotal jaw 44 to pivot away from stationary jaw 34 due to movement of rod 42, as shown in FIGS. 2 and 6 and in dashed lines in FIG. 11. When the jaws are properly positioned on opposite sides of tissue 118 to be sutured, the movable handle member 26 is moved toward the stationary handle member 24 by squeezing the finger and thumb together causing the tissue engaging surfaces 52 and 66 of the jaws to clamp the tissue while needle 56 is forced through the tissue and into opening 65 in pivotal jaw 44. Accordingly, the suture instrument operates as a punch as needle 56 penetrates through the tissue.

After the jaws are operated to punch needle 56 through the tissue 118, suture material 90 is forced through the needle to exit from the open tip of the needle and pass through the opening 65 in pivotal jaw 44, as shown in FIG. 12. To accomplish this, the suture material is fed through inlet 98 of the suture feed mechanism, and the drive roller 80 is rotated clockwise, looking at FIG. 3, with a finger or thumb. The ring 88 engages the suture material which rides in the groove 92 in idler roller 84, and the rollers cooperate to grip and move the suture material. In this manner, the suture material is fed through outlet 100 of the suture feed mechanism and through tubing 104 and needle 56. In practice, the suture material will be fed through the needle and backed off to be adjacent to the needle tip but within the needle prior to insertion of the suturing instrument into the portal 116 such that minimal rotation of drive roller 80 is required to cause a length of the suture material to extend out of needle 56, as shown in FIG. 12.

Once a sufficient length of the suture material is fed through as shown in FIG. 12, the jaws are opened to withdraw the needle back through the tissue; and, the suturing instrument 20 is moved away from the tissue 118 causing a free end segment 122 of the suture material to be folded back on itself, the edge of the aperture 65 in the pivotal jaw 44 catching the suture material to pull the free end segment of the suture material out while the suture material is also fed toward the jaws by driver roller 80 such that the suturing instrument can be withdrawn from the body leaving the suture in place through the tissue as shown in FIG. 14.

With the ends of the suture outside the body, a knot 124 can be tied by the surgeon in any conventional fashion, as shown in FIG. 15; and, the knot can be pushed through the cannula 120 using a throw stick 126 to a position adjacent the tissue 118, as shown in FIG. 16. The knot can now be tightened by pulling on either or both ends of the suture material. Several knots may be tied, and the suture material is then cut with the use of a microsurgical scissors allowing the cut ends of the suture material to be withdrawn through the tube 120.

As will be appreciated from the above, the suturing instrument of the present invention operates as a punch to allow feeding of suture material through tissue to be sutured within the body, knotting the suture material externally of the body and placing and tightening the knot adjacent the tissue without requiring open surgery thereby permitting repair of ligaments and meniscus, among other tissues, arthroscopically.

Inasmuch as the present invention is subject to many variations, modifications and changes in detail, it is intended that all subject matter discussed above or shown in the accompanying drawings be interpreted as illustrative only and not to be taken in a limiting sense.

What is claimed is:
1. A method of arthroscopic suturing of tissue within the body comprising the steps of
  penetrating tissue to be sutured with a hollow needle;
  feeding suture material through the hollow needle to define a free end segment of the suture material extending from the hollow needle;
  withdrawing the hollow needle from the tissue and from the body;
  pulling the free end segment of the suture material from the body;
  tying a knot in the suture material externally of the body; and
  moving the knot into the body to a position adjacent the tissue.

2. A method of arthroscopic suturing of tissue as recited in claim 1 wherein said step of withdrawing the hollow needle from the body and said step of pulling the free end segment of the suture material are performed simultaneously.

3. A method of arthroscopic suturing of tissue within the body comprising the steps of
  inserting a suturing instrument into the body having an elongate tube terminating at a distal end at a jaw tip formed of first and second relatively movable jaws with the first jaw carrying a hollow needle;
  penetrating tissue to be sutured with the hollow needle;
  feeding suture material through the hollow needle to define a free end segment of the suture material extending from the hollow needle;
  withdrawing the hollow needle from the tissue and from the body;
  pulling the free end segment of the suture material from the body;
  tying a knot in the suture material externally of the body; and
  moving the knot into the body to a position adjacent the tissue.

4. A method of arthroscopic suturing as recited in claim 3 wherein the second jaw of the jaw tip has an opening therein to receive the hollow needle when the first and second jaws are closed to cause the hollow needle to penetrate the tissue to be sutured and said step of pulling the free end segment of the suture material from the body includes engaging the free end segment with the edge of the opening in the second jaw.

5. A method of arthroscopic suturing as recited in claim 4 and further comprising the step of clamping the tissue to be sutured with said jaw as said penetrating step is performed.

6. A method of arthroscopic suturing as recited in claim 5 wherein the suturing instrument includes a roller feed mechanism for feeding suture material to the hollow needle and said step of feeding suture material through the hollow needle includes rotating a roller of the roller feed mechanism.

7. A method of suturing tissue in the body comprising the steps of
  inserting an instrument in the body having a distal end carrying first and second relatively movable jaws having openings therein;
  manipulating the jaws to penetrate the tissue to be sutured with at least a portion of one of the jaws and to move the first and second jaws to positions adjacent each other with the openings therein aligned;
  feeding suture material through the openings in the first and second jaws;
  securing ends of the suture material to form a knot; and
  moving the knot to a position adjacent the tissue.

8. A method of suturing tissue as recited in claim 7 wherein the first jaw of the instrument includes a hollow needle and said step of manipulating the jaw means includes penetrating the tissue to be sutured with the hollow needle.

* * * * *

UNITED STATES PATENT AND TRADEMARK OFFICE
CERTIFICATE OF CORRECTION

PATENT NO. : 4,923,461
DATED : May 8, 1990
INVENTOR(S) : Richard B. Caspari et al It is certified that error appears in the above-identified patent and that said Letters Patent is hereby corrected as shown below:

Column 1, line 10, delete "instruments";

line 11, delete "instruments" and replace with --a method--;

line 24, delete "sam" and replace with --same--.

Signed and Sealed this

Sixth Day of August, 1991

Attest:

HARRY F. MANBECK, JR.

*Attesting Officer*        *Commissioner of Patents and Trademarks*

REEXAMINATION CERTIFICATE (2605th)
United States Patent [19]

Caspari et al.

[11] B1 4,923,461

[45] Certificate Issued Jun. 20, 1995

[54] METHOD OF ARTHROSCOPIC SUTURING

[75] Inventors: Richard B. Caspari, Maidens, Va.; Arthur F. Trott, Largo; F. Barry Bays, Seminole, both of Fla.

[73] Assignee: Linvatec Corp., Largo, Fla.

Reexamination Request:
No. 90/003,183, Aug. 27, 1993

Reexamination Certificate for:
Patent No.: 4,923,461
Issued: May 8, 1990
Appl. No.: 326,991
Filed: Mar. 22, 1989

Related U.S. Application Data

[62] Division of Ser. No. 117,158, Nov. 5, 1987, Pat. No. 4,890,615.

[51] Int. Cl.⁶ ............................................. A61B 17/04
[52] U.S. Cl. ................................. 606/146; 606/148
[58] Field of Search .......................... 606/146–148; 128/898

[56] References Cited

PUBLICATIONS

Morgan and Casscells, "Arthroscopic Meniscus Repair: A Safe Approach to the Posterior Horns", The Journal of Arthroscopic and Related Surgery, vol. 2, No. 1, 1986.

*Primary Examiner*—Gary Jackson

[57] ABSTRACT

A method of suturing tissue in the body particularly useful in arthroscopic surgery requiring only small incisions or portals for insertion of diagnostic and surgical instruments includes the steps of inserting an instrument in the body having a distal end carrying relatively movable jaws with openings therein, manipulating the jaws to penetrate the tissue to be sutured and to move the jaws to positions adjacent each other with the openings therein aligned, feeding suture material through the openings in the jaws, securing ends of the suture material to form a knot and moving the knot to a position adjacent the tissue.

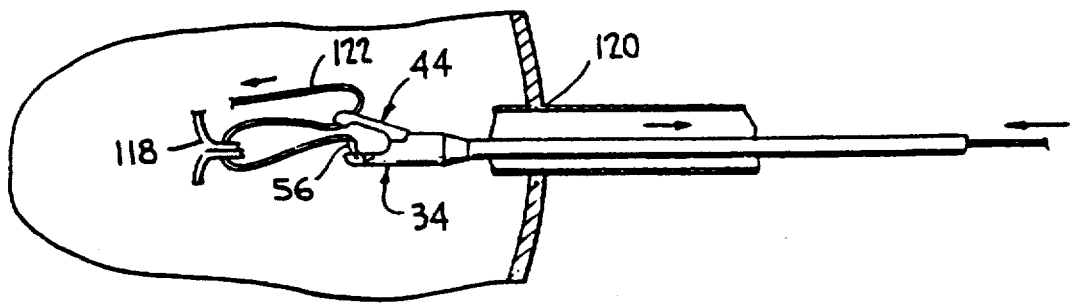

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3–8 is confirmed.

Claims 1 and 2 are determined to be patentable as amended.

New claims 9–12 are added and determined to be patentable.

1. A method of arthroscopic suturing of tissue within the body comprising the steps of:
   penetrating tissue to be sutured with a hollow needle;
   feeding *one end of a single length of* suture material through the hollow needle to define a free end segment of the suture material extending from the hollow needle *through the tissue;*
   withdrawing the hollow needle from the tissue and from the body, *leaving the suture material extending through the tissue;*
   pulling the free end segment of the suture material from the body *toward the other end of the suture material;*
   tying [a knot in] *the ends of* the suture material *together to form a knot* externally of the body; and
   moving the knot into the body to a position adjacent the tissue.

2. A method of arthroscopic suturing of tissue within the body comprising the steps of:
   penetrating the tissue to be sutured with a hollow needle;
   feeding suture material through the hollow needle to define a free end segment of the suture material extending from the hollow needle *through the tissue;*
   withdrawing the hollow needle from the tissue[;], *leaving the suture material extending through the tissue;*
   simultaneously withdrawing the hollow needle from the body while pulling the free end segment of the suture material from the body;
   tying a *moveable* knot in the suture material externally of the body; and
   moving the knot into the body to a position adjacent the tissue.

9. *A method of arthroscopic suturing of tissue within the body comprising the steps of:*
   *penetrating tissue to be sutured with a hollow needle;*
   *feeding a leading end of a length of suture material through the hollow needle and through the tissue to be sutured;*
   *withdrawing the hollow needle from the tissue, leaving the suture material extending through the tissue;*
   *pulling the leading end of the suture material from the body;*
   *feeding suture material through the hollow needle while withdrawing the hollow needle from the body to define a trailing segment of the suture material;*
   *tying the leading end of the suture material and the trailing segment of the suture material together to form a knot in the suture material externally of the body; and*
   *moving the knot into the body to a position adjacent the tissue.*

10. *A method of arthroscopic suturing of tissue within the body comprising the steps of:*
    *penetrating tissue to be sutured with a hollow needle;*
    *advancing a leading end of suture material through the hollow needle and the tissue to be sutured;*
    *withdrawing the leading end of the suture material from the body;*
    *withdrawing the hollow needle from the tissue, leaving the suture material extending through the tissue to form a trailing end of the suture material;*
    *tying the leading end and the trailing end of the suture material together to form a knot externally of the body; and*
    *moving the knot into the body to a position adjacent the tissue.*

11. *The method of arthroscopic suturing of tissue within the body of claims 1, 2, 9, or 10 wherein the knot is pushed into the body to a position adjacent the tissue.*

12. *The method of arthroscopic suturing of tissue as recited in claim 1 wherein said step of withdrawing the hollow needle from the body and said step of pulling the free end segment of the suture material are performed simultaneously.*

* * * * *